(12) United States Patent
Kuramori et al.

(10) Patent No.: US 7,486,987 B2
(45) Date of Patent: Feb. 3, 2009

(54) WORK COMFORT EVALUATING DEVICE AND WORK COMFORT EVALUATING METHOD

(75) Inventors: Akira Kuramori, Kanagawa (JP); Noritaka Koguchi, Kanagawa (JP); Masayoshi Kamijo, Nagano (JP); Tsugutake Sadoyama, Ibaraki (JP)

(73) Assignee: The Yokohama Rubber Co., Ltd., Tokyo (JP)

(*) Notice: Subject to any disclaimer, the term of this patent is extended or adjusted under 35 U.S.C. 154(b) by 192 days.

(21) Appl. No.: 10/942,045

(22) Filed: Sep. 16, 2004

(65) Prior Publication Data

US 2005/0080350 A1 Apr. 14, 2005

(30) Foreign Application Priority Data

Sep. 17, 2003 (JP) ............... 2003-325042

(51) Int. Cl.
*A61B 5/04* (2006.01)
*G08B 23/00* (2006.01)
*B62D 49/06* (2006.01)

(52) U.S. Cl. .................. 600/546; 340/576; 180/313

(58) Field of Classification Search .......... 600/546; 180/313; 340/576
See application file for complete search history.

(56) References Cited

U.S. PATENT DOCUMENTS

| | | | |
|---|---|---|---|
| 4,667,513 A | | 5/1987 | Konno |
| 5,740,813 A | * | 4/1998 | Ogata et al. ........... 600/546 |
| 5,964,719 A | | 10/1999 | Costello et al. |
| 6,004,312 A | * | 12/1999 | Finneran et al. ....... 600/546 |
| 6,061,610 A | * | 5/2000 | Boer ....................... 701/1 |
| 6,265,978 B1 | * | 7/2001 | Atlas ..................... 340/575 |
| 6,974,414 B2 | * | 12/2005 | Victor .................... 600/300 |

(Continued)

FOREIGN PATENT DOCUMENTS

JP 2002-214083 7/2002

(Continued)

OTHER PUBLICATIONS

English machine translation of JP 2004-049622. Obtained Sep. 18, 2008. Japan Patent Office. <http://www.jpo.go.jp>. pp. 1-12.*

(Continued)

*Primary Examiner*—Max Hindenburg
*Assistant Examiner*—John Pani
(74) *Attorney, Agent, or Firm*—Finnegan, Henderson, Farabow, Garrett & Dunner, L.L.P.

(57) ABSTRACT

A work comfort evaluating device is a device for evaluating a level of comfort of work by measuring myoelectric potentials of plural muscles when the work is done by antagonistic activities of the muscles. The device has a pair of detecting sensors, an amplifier, a signal processing part, a work-load intensity calculating part, and an evaluation part. The sensors sense myoelectric potentials of the muscles at a time of the work. The signal processing part calculates a synchronous contraction intensity of the muscles by using myoelectric potential waveforms. The work-load intensity calculating part calculates a level of a work load intensity in the work. The evaluation part evaluates a level of comfort of the work by normalizing the synchronous contraction intensity by the level of the work load intensity calculated.

13 Claims, 5 Drawing Sheets

U.S. PATENT DOCUMENTS

2004/0088205 A1* 5/2004 Geisler et al. .................. 705/7
2005/0015016 A1* 1/2005 Elitok et al. ................. 600/544

FOREIGN PATENT DOCUMENTS

| JP | 2002-225585 | | 8/2002 |
|---|---|---|---|
| JP | 2002-230699 | * | 8/2002 |
| JP | 2002230699 | | 8/2002 |
| JP | 2003 177079 | | 6/2003 |
| JP | 2003-1777079 | | 6/2003 |
| JP | 2004-049622 | | 2/2004 |
| JP | 2004049622 A | * | 2/2004 |

OTHER PUBLICATIONS

Jennifer A. Healey, "Wearable and Automotive Systems for Affect Recognition from Physiology", Submitted to the Department of Electrical Engineering and Computer Science in partial fulfillment of the requirements for the degree of Doctor of Philosophy at the Massachusetts Institute of Technology, May 2000.

Helenice Gil Coury, Shrawan Kumar, and Yogesh Narayan, "An Electromyographic study of Upper Limb Adduction Force with Varying Shoulder and Elbow Postures", Journal of Electromyography and Kineslology, vol. 8, pp. 157-168.

Lehman, G.J., et al., "The Importance of Normalization in the Interpretation of Surface Electromyography: A Proof of Principle," *J. Manip. Physiol. Therapeut.* 22:444-46 (1999).

Tanaka, J. et al., "Workload of Using a Driver Assistance System," *IEEE Intelligent Transportation Systems Conference Proceedings* pp. 382-386 (2000).

Yoshikawa, M. et al., "Measurement of Physical and Mental Reactions of Drivers During Driving," 11th Lecture on Measurement and Control Research in Shinshu Area, Collected Papers, Jun. 15, 1998.

* cited by examiner

FIG. 2
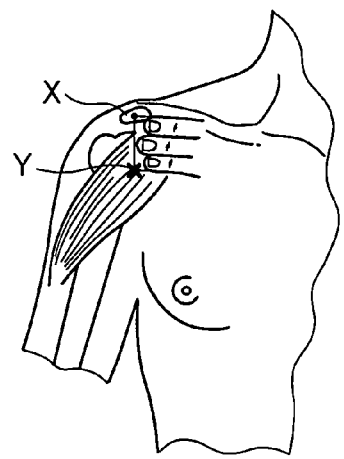
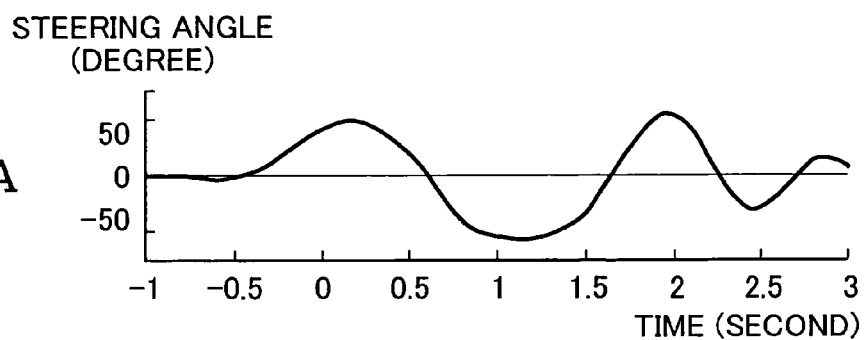
FIG. 3A
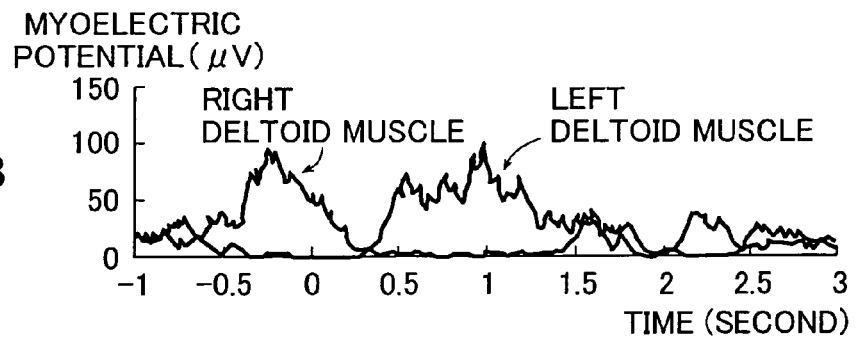
FIG. 3B
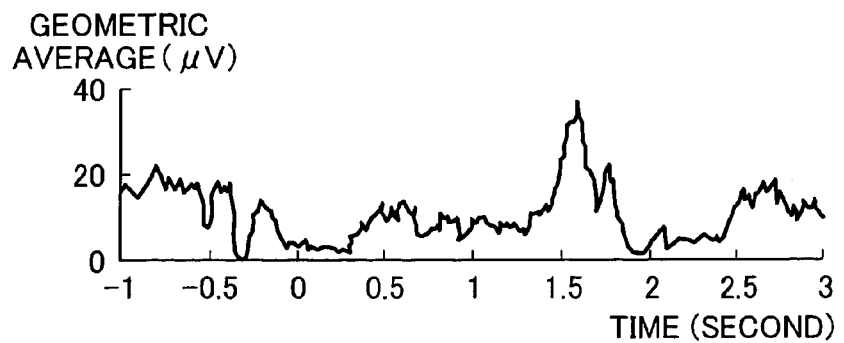
FIG. 3C

WORK COMFORT EVALUATING DEVICE AND WORK COMFORT EVALUATING METHOD

BACKGROUND OF THE INVENTION

The present invention relates to a work comfort evaluating device and method for evaluating a level of comfort of work by measuring myoelectric potentials of plural deltoid muscles when the work is done by antagonistic activities of the deltoid muscles. More particularly, the invention relates to a device and method for evaluating a steering comfort of a vehicle.

At present, automobile manufacturers and tire manufacturers pursue steering easiness of a vehicle and develop vehicles and tires by using various methods in order to provide such vehicles as automobiles, and tires, which ensure comfortable steering operations. In the development of the vehicles and tires, a steering comfort is evaluated, in most cases, by using a subjective sensory evaluation of a driver, or by using a method in which physical measurement data representing a behavior of the vehicle is acquired by using a measuring sensor such as an acceleration sensor that is attached to the vehicle, and the vehicle behavior is quantitatively measured.

To evaluate a level of work load imparted when given work is done, an electromyogram depicting signal waveforms of myoelectric potentials of a worker is used, and loads imparted to the muscles of the worker are quantitatively grasped. Since the measurement itself of the myoelectric potential is simple and good in its adaptation, it is thought that a level of the work load imparted when given work is done can properly be evaluated when the electromyogram is used. Further, there is a possibility that the evaluating method using the electromyogram is applied to the steering operation of the vehicle by the driver.

JP 2002-225585 A discloses a technique in which a myoelectric potential of a muscle acting to extend the arm and a myoelectric potential of another muscle acting to contract the arm are both measured, a value (conflict value) concerning a conflict of those two myoelectric potentials is calculated, and a level of driving load on the driver is determined based on the conflict value. More specifically, myoelectric potentials of the muscles of the driver which conflictingly act are measured by using myoelectric potential sensors, and a conflict feature quantity is calculated from a conflict value of the myoelectric potentials measured. When the calculated conflict feature quantity exceeds a predetermined threshold value, it is judged that the driving load on the driver has increased (paragraphs [0031] to [0038] in JP 2002-225585 A).

To obtain the threshold value used for the judgment, as shown in FIG. 10 in JP 2002-225585 A, the myoelectric potentials are measured for a long time, for example, 10 minutes, 8 minutes or 5 minutes, and a conflict value is calculated based on the measurement results. A conflict feature quantity for calibration, such as maximum values and average values, is calculated from the conflict value obtained by the long-time measurement. The threshold value in question is determined by multiplying the calculated feature quantity by a preset coefficient. Thus, to determine the threshold value, the long time measurement of 10 minutes, for example, is required. During this measurement time, the driving load on the driver cannot be judged. To cope with this, in JP 2002-225585 A, the data of the previous driving by the driver is used as a reference (paragraph [0040] in JP 2002-225585 A).

It is known that the myoelectric potential level frequently takes a different value when the myoelectric potential is measured because every time the sensors are stuck onto parts of the muscles before the measurement. If the data of the previous driving is used, which contains the myoelectric potential level that is probably different from the level of the current measurement, the judgment of the driving load on the driver will be erroneous. That is, the conflict feature quantity for calibration, which is used for determining the threshold value, is calculated from the myoelectric potential which will take a different value every time the detecting sensors are stuck. As a result, the conflict feature quantity for calibration also takes a different value every time the sensors are stuck. Accordingly, if the threshold value is determined by multiplying the conflict feature quantity for calibration by a fixed coefficient, judgment of the driving load on the driver will be erroneous.

The driving load on the driver disclosed in JP 2002-225585 A is a combination of a mental burden as to whether the driving is easy for the driver and a physical load when the driver actually drives. Accordingly, in a case where a large steering force is required for operating the steering wheel depending on the type of tires mounted, the physical load imparted to the steering wheel is large and the driving load increases. In this case, the steering force is large and a stable steering is secured, giving the driver a sense of safety and making the mental load less. However, the increase of the steering force results in an increase of the driving load.

In JP 2002-225585 A, the driving load on the driver is evaluated by using threshold values preset for respective running modes of high-speed cruising, highway congestion and city-area driving. Therefore, it is impossible to know a difference of the driving load caused by the mental burden on the drive in the high-speed cruising mode from the mental load in the highway congestion mode.

Such problems also occur not only in the evaluation of the steering operation of the vehicle but also in a case where a comfort is evaluated at work where an object to be operated is operated by antagonistically activating plural muscles (a pair of muscles, for example) of a human body.

SUMMARY OF THE INVENTION

Accordingly, an object of the present invention is to provide a work comfort evaluating device and method for evaluating a level of comfort of work by measuring myoelectric potentials of muscles when the work is done by antagonistic activities of the muscles, with which a level of comfort of work can be quantitatively evaluated from short-time measurement results.

The present invention provides a work comfort evaluating device for evaluating a level of comfort of work by measuring myoelectric potentials of muscles when the work is done by antagonistic activities of the muscles. The work comfort evaluating device comprises: a pair of detecting sensors for sensing myoelectric potentials of the muscles, said myoelectric potentials generated through muscular activities of a human body at a time of work; an amplifier for amplifying the myoelectric potentials sensed by the detecting sensors; a signal processing part for calculating a synchronous contraction intensity of the muscles by using myoelectric potential waveforms of the amplified myoelectric potentials; a work load intensity calculating part for calculating a level of a work load intensity in the work imparting load to the muscles at a time of the generation of the synchronous contraction intensity; and an evaluation part for evaluating a level of comfort of the work by normalizing the synchronous contraction intensity by using the level of the work load intensity calculated.

Note that the antagonistic activities of the muscles generally means that one muscle contracts while the other relaxes if there are two muscles cooperatively act to perform a piece of work.

The muscles are preferably a pair of muscles located at right and left parts of the human body. More preferably, the pair of muscles are deltoid muscles of a shoulder of the human body.

The work load intensity calculating part preferably calculates a level of the work load intensity from the myoelectric potential waveforms of the muscles. Then, the work load intensity calculating part more preferably calculates intensities of muscular loads imparted to the muscles in the work from the myoelectric potential waveforms of the muscles, and averages and smoothes the calculated muscular load intensities in an averaging process to thereby calculate the level of the work load intensity. Then, the averaging process may be a geometric averaging process.

In the work comfort evaluating device, the work is preferably a work in which the muscles cooperate to cause an object to be operated to dynamically behave, and the work load intensity calculating part preferably calculate a level of the work load intensity by measuring a physical quantity representing a dynamic behavior of the object operated by the work.

The signal processing part preferably calculates a geometrical average of the myoelectric potential waveforms of the muscles, and calculates root mean square values of the calculated geometrical average within a predetermined period, whereby the synchronous contraction intensity is generated.

The work may be a driving of a vehicle that is performed by a driver turning a steering wheel.

The invention also provides a work comfort evaluating method for evaluating a level of comfort of a work by measuring myoelectric potentials of muscles when the work is done by antagonistic activities of the muscles. The work comfort evaluating method comprises: sensing and amplifying myoelectric potentials of the muscles generated through muscular activities of a human body at a time of work; generating a synchronous contraction intensity of the muscles by using myoelectric potential waveforms of the amplified myoelectric potentials; calculating a level of a work load intensity in the work imparting load to the muscles at a time of the generation of the synchronous contraction intensity; and evaluating a level of comfort of the work by normalizing the synchronous contraction intensity by the level of the work load intensity calculated.

In the present invention, where myoelectric potentials of muscles of antagonistic activities are measured and a synchronous contraction intensity is calculated from a synchronous contraction waveform of the myoelectric potentials with a work-load intensity, a level of comfort of work can be quantitatively evaluated from short-time measurement results.

Therefore, the present invention which evaluates a work comfort by a level of mental stress from the short-time measurement results, does not have to take a longer time, for example 10 minutes, before a work comfort is evaluated, compared to a conventional method. Specifically, the present invention normalizes the synchronous contraction intensity by the level of the work load intensity, thereby a rate of synchronous contraction intensity which increases as the mental stress is stronger, in the work-load intensity is obtained. Using the ratio, a work comfort of driver's steering operation can be evaluated irrespective of various driving modes, a high-speed cruising mode, highway congestion mode, city-area driving mode and so on.

This application claims priority on Japanese patent application No.2003-325042, the entire contents of which are hereby incorporated by reference.

BRIEF DESCRIPTION OF THE DRAWINGS

A work comfort evaluating device and a work comfort evaluating method, which are believed to be the best modes when the present invention is carried out, will be described with reference to the accompanying drawings.

In the accompanying drawings:

FIG. 2 is a diagram explaining a deltoid muscle a myoelectric potential of which is to be measured in the steering comfort evaluating device shown in FIG. 1;

FIGS. 3A to 3C are graphs showing waveform data acquired by the steering comfort evaluating device shown in FIG. 1;

DESCRIPTION OF THE PREFFERD EMBODIMENT

Figure 1:
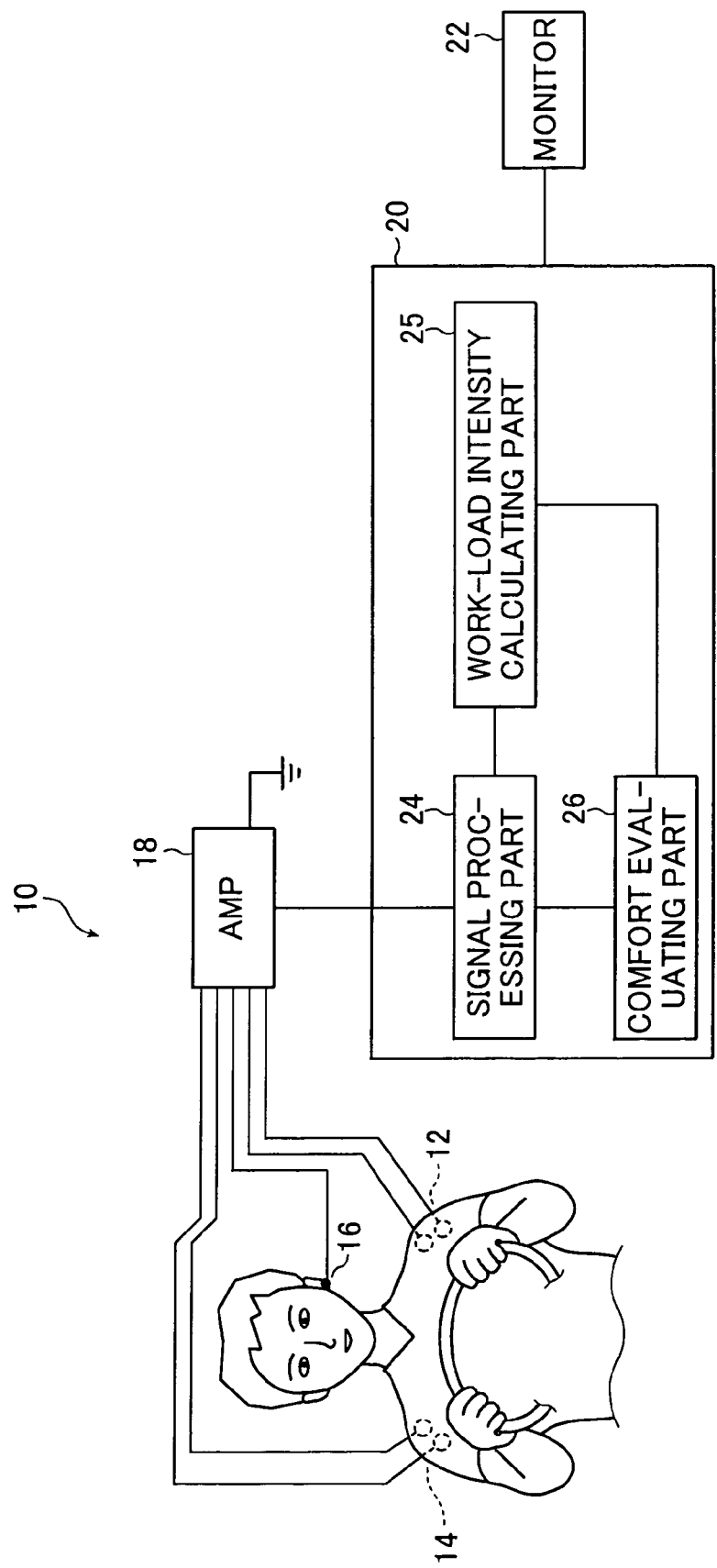
FIG. 1 is a schematic block diagram showing a steering comfort evaluating device as a work comfort evaluating device of the invention applied to a driver's steering operation.

FIG. 1 is a schematic block diagram showing a steering comfort evaluating device 10 as a work comfort evaluating device of the invention applied to a driver's steering operation.

The steering comfort evaluating device 10 is a device for evaluating a level of comfort of steering operation by a driver who drives a vehicle. The steering comfort evaluating device 10 is made up of myoelectric potential detecting sensors 12 and 14 for detecting myoelectric potentials at right and left deltoid muscles of the driver, an electrode 16, an amplifier 18 for amplifying myoelectric potentials derived from the potential detecting sensors 12 and 14, a processor unit 20 for evaluating a level of steering comfort based on time-series waveforms of the amplified myoelectric potentials at the right and left deltoid muscles, and a monitor 22 for monitoring the result of the evaluation.

The myoelectric potential detecting sensor 12 is a sensor for sensing a myoelectric potential of the deltoid muscle of the left shoulder of the driver. The detecting sensor 12 is formed with a pair of Ag/AgCl dish-shaped electrodes. Those paired electrodes are stuck onto a surface part of the left shoulder where the deltoid muscle is located, while being spaced apart from each other a predetermined distance of several milimeters, for example, 5 mm.

The myoelectric potential detecting sensor 14 is a sensor for detecting a myoelectric potential of the deltoid muscle of the right shoulder of the driver. The detecting sensor 14, like the detecting sensor 12, is formed with a pair of Ag/Ag CL dish-shaped electrodes. Those paired electrodes are stuck onto a surface part of the right shoulder where the deltoid muscle is located, while being spaced apart from each other a predetermined distance of several milimeters, for example, 5 mm.

A material for those potential detecting sensors 12 and 14 is not limited to Ag/Ag CL, but may be any of other suitable materials, such as Ag or stainless steel.

Before the electrodes of those detecting sensors are stuck onto the skin surface of the driver, each electrode is scrubbed with a suitable means, and cleaned by using alcohol, and then are attached to the skin surface by using electrode paste. In this case, the cleaning operation is continued till an electric resistance is reduced to 30 kΩ (preferably 5 kΩ). The paired electrodes are attached onto a venter of the muscle in a state where those electrodes are arranged in parallel with the muscular fiber. As shown in FIG. 2, the electrodes are attached to positions Y spaced in a longitudinal direction of the arm from an end X of the outer side of the clavicle by a distance corresponding to three fingers put together, with the predetermined distance left between those electrodes.

The electrode 16 is an ground electrode to be attached to an earlobe of the driver, which is an electrically inactive position, in order to keep a potential of the driver constant. Use of the electrode 16 ensures an exact measurement carried out by the potential detecting sensors 12 and 14. The electrode 16, connected to the amplifier 18, is grounded via the amplifier 18.

The amplifier 18 is connected to the detecting sensors 12 and 14 by means of lead wires. The amplifier is a known operational amplifier for amplifying myoelectric potentials detected by the detecting sensors 12 and 14.

The myoelectric potentials, which are detected by the detecting sensors 12 and 14 and amplified by the amplifier, are transmitted to the processor unit 20.

The processor unit 20 contains a signal processing part 24, a work load intensity calculating part 25, and a comfort evaluating part 26.

The processor unit 20 is a unit containing a computer. The signal processing part 24, the work load intensity calculating part 25, and the comfort evaluating part 26 exhibit their own functions when the program is executed.

The signal processing part 24, the work load intensity calculating part 25, and the comfort evaluating part 26 may be constructed with dedicated circuits.

The signal processing part 24 samples time-series data of myoelectric potentials at the two deltoid muscles to generate myoelectric potential waveforms and calculates a synchronous contraction intensity by using the myoelectric potential waveforms.

Specifically, the time-series data of the myoelectric potentials are sampled and subjected to full-wave rectification. The rectified waveforms are smoothed by smoothing filters (low-pass filters) to generate signal waveforms of the myoelectric potentials (myoelectric potential waveforms). A geometric average (a square root of the product of the myoelectric potential waveforms) of the two myoelectric potential waveforms at the same time point is calculated. A synchronous contraction waveform generated when the right and left deltoid muscles simultaneously and synchronously contract is formed by using the average values thus obtained. Further, a root means square (RMS) of the synchronous contraction waveform is calculated, and the calculated RMS is used as a synchronous contraction intensity. The RMS value is a square root of the sum of squares of the deviation of the waveforms from the mean value (simple addition mean value) during a predetermined period. The predetermined period is, for example, 0.5 to 10 seconds. It is evident that the synchronous contraction waveform in the present invention is not limited to the waveform generated by calculating a geometric average of the two myoelectric potential waveforms. For example, the myoelectric potential waveform that is the smaller in value of the two myoelectric potential waveforms may be used for the synchronous contraction waveform. However, it is preferable to generate the synchronous contraction waveform by calculating a geometric average of the two myoelectric potential waveforms, with an intention of lessening deterioration of the synchronous contraction waveform, where the deterioration arises from a level variation of the myoelectric potential caused every time the potential detecting sensors 12 and 14 are stuck.

The signal processing part 24 supplies to the work load intensity calculating part 25 the signal waveforms of the myoelectric potentials, which are formed through the smoothing process.

FIG. 3A typically shows time-series data of steering angles produced when a driver turns the steering wheel. FIG. 3B shows myoelectric potential waveforms of the right and left deltoid muscles of the driver, which are formed by performing full-wave rectification on the myoelectric potential waveforms and smoothing them by smoothing filters. The myoelectric potential signal originally contains high frequency components generated when the muscle contracts. However, a force generated when the muscle contracts does not contain high frequency components. The reason for performing full-wave rectification on and smoothing the myoelectric potential waveforms is to make the myoelectric potential waveforms correspond to the force generated when the muscle contracts. FIG. 3C shows a synchronous contraction waveform that is obtained by calculating a geometric average of the myoelectric potential waveforms of the right and left deltoid muscles shown in FIG. 3B. An RMS value of the synchronous contraction waveform for a predetermined period is calculated, whereby a synchronous contraction intensity is obtained.

The work load intensity calculating part 25 calculates a level of the work load intensity in the steering operation by the driver by using the myoelectric potential waveforms supplied from the signal processing part 24. Specifically, muscular load intensities of the right and left deltoid muscles when the driver operates the steering wheel are calculated from the myoelectric potential waveforms. Those muscular load intensities are averaged. A level of work load intensity is calculated together with the calculation of a synchronous contraction intensity. The calculation of the work load intensity is performed together with the generation of the synchronous contraction intensity. The muscular load intensity is obtained by calculating an RMS value of the myoelectric potential waveform of each of the right and left deltoid muscles as shown in FIG. 3B. Work-load intensities of the right and left deltoid muscles when those deltoid muscles engage in the steering operation are calculated by averaging the muscular load intensities of the right and left deltoid muscles. The work load intensity is obtained by calculating separately the muscular load intensities of the right and left deltoid muscles and averaging those calculated ones. The averaging process is not limited to the geometric average process, but may be a normal average (simple addition mean) process; however, the geometric average process is preferable from the point of view of the accuracy.

The work load intensity calculated is supplied to the comfort evaluating part 26.

The comfort evaluating part 26 calculates a synchronous contraction rate, which represents a level of a driver's mental stress by using the synchronous contraction intensities and the work load intensity, which are supplied from the signal processing part 24 and the work load intensity calculating part 25, and evaluates a level of comfort of the driver's steering operation based on the synchronous contraction rate.

Thus, the synchronous contraction rate to be calculated represents a ratio of the synchronous contraction intensity which indicates a mental stress for the work load intensity when the synchronous contraction intensity representing a level of the mental stress is normalized by dividing the synchronous contraction intensity by the work load intensity.

An evaluation of the driver's comfort in the steering operation is performed in the following manner, for example. Comfort levels of the driver when he/she operates the steering wheel are arranged in ranks. A synchronous contraction rate calculated is compared with preset values for the respective ranks. The comfort level is evaluated based on the comparison result. An evaluation of the driver's comfort in the steering operation may also be performed in the following manner, for example. A frequency at which the synchronous contraction rate falls within a predetermined segment within a predetermined time is compared with the frequencies preset to rank comfort levels of the steering operation by the driver. The comfort level is evaluated based on the comparison result.

Such evaluation results, together with the calculation results of the myoelectric potential waveforms, the synchronous contraction waveforms, the muscular load intensities or the work load intensity, and the like, are sent to the monitor 22 to be displayed.

As described above, the steering comfort evaluating device 10 calculates a synchronous contraction waveform from the myoelectric potential waveforms of the right and left deltoid muscles, and calculates a synchronous contraction intensity. Further, the steering comfort evaluating device calculates a work load intensity from the myoelectric potential waveforms. The steering comfort evaluating device also calculates a synchronous contraction rate representing a level of mental stress of the driver when he/she operates the steering wheel, by using the calculated synchronous contraction intensity and the work load intensity. Finally, the steering a level of comfort evaluating device evaluates a level of steering comfort of the driver based on the synchronous contraction rate.

To steer the vehicle, generally, the driver turns the steering wheel. To steer the vehicle to the right, the driver angularly moves the left hand gripping the wheel in an upward direction. At this time, the deltoid muscle of the driver's left shoulder contracts actively. On the other hand, the right hand of the driver is merely put on the steering wheel and moves passively. Accordingly, at this time, the deltoid muscle of the right shoulder relaxes. When steering the vehicle to the left, the deltoid muscle of the driver's left shoulder relaxes, while the deltoid muscle of the right shoulder contracts. Thus, the steering operation is performed by the driver in such a manner that one of the right and left deltoid muscles of the human body, which are symmetrically disposed as laterally viewed, contracts, while the other relaxes. That is, the steering operation is done that is antagonistically done by the paired muscles that are laterally symmetrical.

However, there is a case where the driver grips the steering wheel by excessive force for handling because the driver has some mental burden when the driver is hindered from smooth steering operation and incessantly grips the steering wheel in a strained condition, for example. There is also a case where the steering operation is difficult and the driver strains himself. In such cases, the right and left deltoid muscles synchronous contract also in the steering operation that is done through the antagonistic activities of the right and left deltoid muscles. In this way, of the paired muscles that antagonistically act, one muscle contracts when it should relax, simultaneously with the straining state of the other muscle that should be strained. In this case, the one muscle generates a myoelectric potential. A waveform of this myoelectric potential is called a synchronous contraction waveform.

A force by which the driver grips the steering wheel in the above situation is produced as the result of such activities of the deltoid muscles. However, this wheel gripping force cannot be obtained from measurement data of physical quantities representing a behavior of the vehicle, which are measured by measuring sensors such as acceleration sensors and load cells.

The inventors of the present invention found the fact that steering easiness of the vehicle and controllability of the vehicle by the steering operation can be evaluated by normalizing the intensity or frequency of the synchronous contraction by using the work load intensity.

The calculation for obtaining the work load intensity in the steering operation done by the driver is not limited to the calculation using the myoelectric potentials at the right and left deltoid muscles. The steering comfort evaluating device 10 may take any configuration if the muscles antagonistically used in the steering operation are used as objects of which myoelectric potentials are to be measured. For example, the biceps brachii muscle and the triceps brachii muscle may be treated as the paired muscles that antagonistically act, and used as the objects of which myoelectric potentials are to be measured. Plural pairs of antagonistically acting muscles may be used. In this case, the myoelectric potentials of those muscle pairs may be measured in the following manner. Those muscle pairs are classified into two groups: one group consisting of muscles which simultaneously contract, and the other group consisting of muscles which simultaneously relax. The myoelectric potentials of those muscles of each group are multiplied or averaged to thereby form two myoelectric potential waveforms. The thus obtained myoelectric potential waveforms of those two groups are handled similarly to the right and left deltoid muscle waveforms as already described, to thereby calculate the synchronous contraction rate.

While the work load intensity is calculated by using the myoelectric potentials of the muscles in the embodiment described above, it may be calculated in any of other suitable ways. In the steering operation where a plurality of muscles cooperatively act to turn the steering wheel, a steering torque of the steering wheel is measured and a steering angular velocity is measured in addition to the steering torque, thereby to calculate a steering operation energy based on the measurement value or values. The steering torque or the operation energy may be used as the work load intensity. Alternatively, a lateral acceleration or a yaw angular velocity of the vehicle, which are generated when the steering wheel is turned, is measured. The result of the measurement is used as the work load intensity in the steering operation. In this way, in the present invention, at work in which a plurality of muscles cooperate to cause an object to be operated, such as a steering wheel or a vehicle, to dynamically behave, the work load intensity calculating part 25 may calculate a work load intensity by measuring physical quantities representing a dynamic behavior of the object (the steering wheel, the vehicle, or the like) which has been operated.

Figure 4:
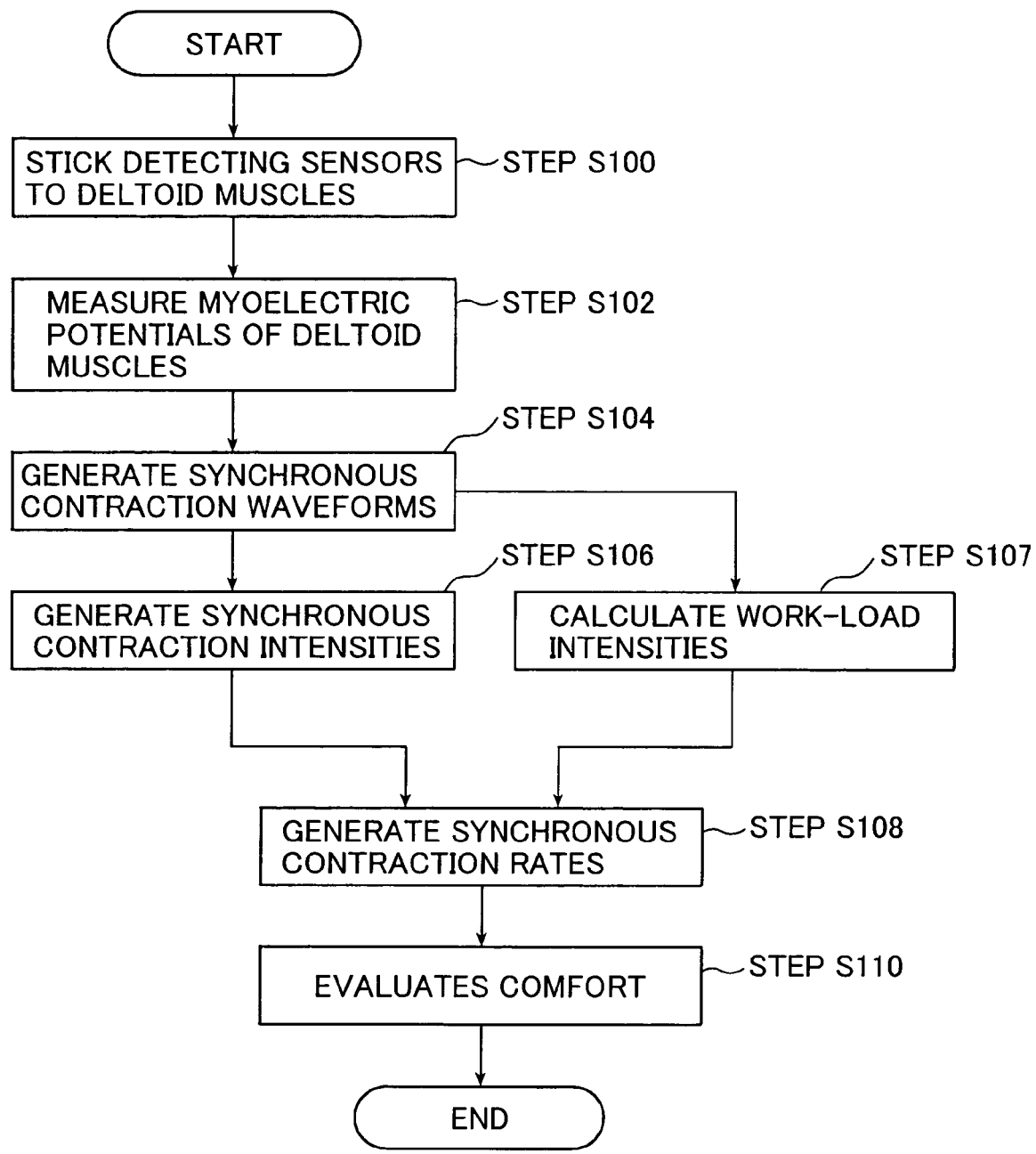
FIG. 4 is a flow chart showing steps in a steering comfort evaluating method according to the present invention.

FIG. 4 is a flow chart showing steps for evaluating a level of steering comfort of a driver in a steering comfort evaluating method according to the present invention.

To start with, the myoelectric potential detecting sensors 12 and 14 are stuck onto surface parts of the right and left shoulders where the right and left deltoid muscles of the driver are located (step 100). At the same time, the electrode 16 is stuck onto the earlobe of the driver.

After the sticking of the potential detecting sensors 12 and 14, myoelectric potentials at the right and left deltoid muscles of the driver in driving are measured (step S102).

Then, signals of the myoelectric potentials acquired by the myoelectric potential measurement are sampled, A/D converted, and subjected to full-wave rectification, and thereafter smoothed by the smoothing filters (low-pass filters) to thereby form myoelectric potential waveforms of the right and left deltoid muscles as shown in FIG. 3B (step S104). The reason for performing full-wave rectification on and smoothing the myoelectric potential waveforms is to make the myoelectric potential waveforms correspond to the force generated when the muscle contracts, because the myoelectric potential signals are signals containing high frequency components.

The generated myoelectric potential waveforms of the right and left deltoid muscles are averaged to thereby form a synchronous contraction waveform as shown in FIG. 3C (step S104). A geometric averaging process, for example, is preferably used for the averaging process. The geometric averaging process is carried out by calculating a square root of the product of the right and left deltoid muscle waveforms. Therefore, the geometric average of the myoelectric potential waveform of small level and the waveform of large level is more affected by the myoelectric potential waveform of the small level and the average value is small. The small value indicates a level of contraction of the muscle owing to mental stress although the muscle should not contract. In the present invention, the synchronous contraction waveform can efficiently be calculated by utilizing the geometric average process. The synchronous contraction waveform in the present invention is not limited to the waveform calculated by using the geometric average. For example, the two myoelectric potential waveforms may be compared, and the myoelectric potential waveform having the smaller values may be used as the synchronous contraction waveform. Then, an RMS value of the synchronous contraction waveform is calculated for the synchronous contraction intensity (step S106). The RMS value is calculated at an interval of 0.1 to 0.5 second.

Work load intensities of the right and left deltoid muscles by using the myoelectric potential waveforms are calculated (step S107). The work load intensity is obtained by calculating the muscular load intensities of the right and left deltoid muscles by using the myoelectric potential waveforms of those muscles and averaging the calculated muscular load intensities. The muscular load intensity is an RMS value of the myoelectric potential waveform, for example, and the averaging process is a geometric averaging process. Thus, in the invention, the work load intensity is obtained by calculating the muscular load intensities of the right and left deltoid muscles and averaging the calculated muscular loads. The work load intensity may also be obtained in the following manner. When the driver operates a specific object to be operated, such as a steering wheel, physical quantities representing a dynamic behavior of the object having been operated is measured, and the result of the measurement is used as the work load intensity.

As described above, an RMS value is calculated to obtain the synchronous contraction intensity, and another RMS value is calculated to obtain the muscular load intensity. It is preferable that those two RMS values are obtained within the same period of time.

A synchronous contraction rate is calculated by using the thus calculated synchronous contraction intensity and the work load intensity (step S108). The calculated synchronous contraction rate is a rate obtained when the synchronous contraction intensity is normalized by dividing it by the work load intensity. This rate is a rate of the synchronous contraction rate representative of an intensity versus an intensity at which each muscle receives work load, where the muscles, which do not contract normally, simultaneously and synchronously contract because of mental stress. Therefore, it is evaluated that when the synchronous contraction rate is large, the driver works with great mental stress.

Next, a level of comfort representing a level of the mental stress is evaluated by using such a synchronous contraction rate (step S110). In the present invention, a method of evaluating the level of comfort by using the synchronous contraction rate is not specifically limited. For example, the level of comfort may be directly evaluated by using a value of the synchronous contraction rate. In another method, levels of comfort for work to be done are arranged in several ranks. A threshold value of the synchronous contraction rate is set for each comfort level. When a calculated synchronous contraction rate within the threshold value continues for a predetermined period, it is evaluated that the comfort level of the work is within the threshold value.

As described above, in the present invention, plural myoelectric potentials of the muscles that antagonistically act, such as the right and left deltoid muscles, are measured, and the level of comfort of the driver that changes when he/she operates the steering wheel can be evaluated based on the result of the measurement that is performed for a short time.

Figure 5:
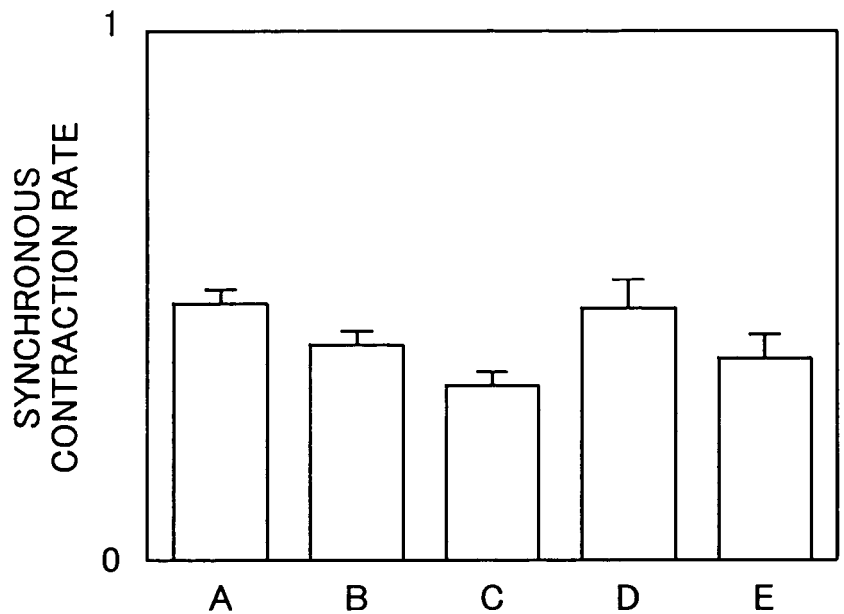
FIG. 5 is a graph showing some examples of results of synchronous contraction rates calculated by the steering comfort evaluating device shown in FIG. 1.

FIG. 5 shows average values and standard deviations of the synchronous contraction rates when the driver drives a 2-liter sedan type car with various types of tires mounted thereon and changes lanes on the road. Measurement was repeated five times.

The abscissa of a graph of FIG. 5 represents test specifications A to E when the driver performed lane-changing with various types of tires. The test specifications A to E will be described later.

When changing the lanes, the car ran at a speed of 100 km/hour, and was laterally shifted by 4 m. The synchronous contraction rates in FIG. 5 are RMS values for 4 seconds in each lane-changing. Three types of tires (NVH, STL, and HPT) shown in Table 1 below were used for mounting on the car. The same type of tires were mounted on the front and rear wheels, or different types of tires were mounted on the front wheels and the rear wheels, to provide five combinations of tires as the test specifications which were tested as shown in Table 2 below. In the table, NVH indicates a tire which is designed exclusively for securing a good ride, and is excellent in noise characteristic, vibration characteristic, and harshness characteristic. STL indicates a studless tire. HTP indicates a tire having a good drivability. Table 1 further contains a size of each tire type, a cornering power $CP_f$ at a front wheel load of the vehicle when the tires are mounted, and another cornering power $CP_r$ at a rear wheel load.

Table 2 shows five test specifications (A to E) based on combinations of three types of tires, NVH, STL, and HPT. In each of the test specifications A to C, the same type of tires are mounted on the front wheel and the rear wheel. In the test specification D, tires of the HPT type are mounted on the front wheels, and tires of the NVH type are mounted on the rear wheels. In the test specification E, tires of the NVH type are mounted on the front wheels, and tires of the HPT type are mounted on the rear wheels. The types of tires mounted on the front wheels and on the rear wheels are different in the test specification D and E, so as to change the steering characteristic. The steering characteristic in the test specification D is found oversteering compared to the test specifications A to C. The steering characteristic in the test specification E is found understeering compared to the test specifications A to C. As seen from FIG. 5, the synchronous contraction rate in the test specification C is the smallest of all the synchronous contraction rates in the test specifications, and that in the test specification D is the largest

TABLE 1

| Tire type | Size | $CP_f$ | $CP_r$ |
| --- | --- | --- | --- |
| NVH | 195/65R15 91H | 1.20(KN/deg) | 1.16(KN/deg) |
| STL | 205/55R15 89Q | 0.94 | 0.91 |
| HPT | 205/55R16 89V | 1.81 | 1.75 |

TABLE 2

| Test Specification | front wheels/Rear wheels |
| --- | --- |
| A | NVH/NVH |
| B | STL/STL |
| C | HPT/HPT |
| D | HPT/NVH |
| E | NVH/HPT |

Figure 6:
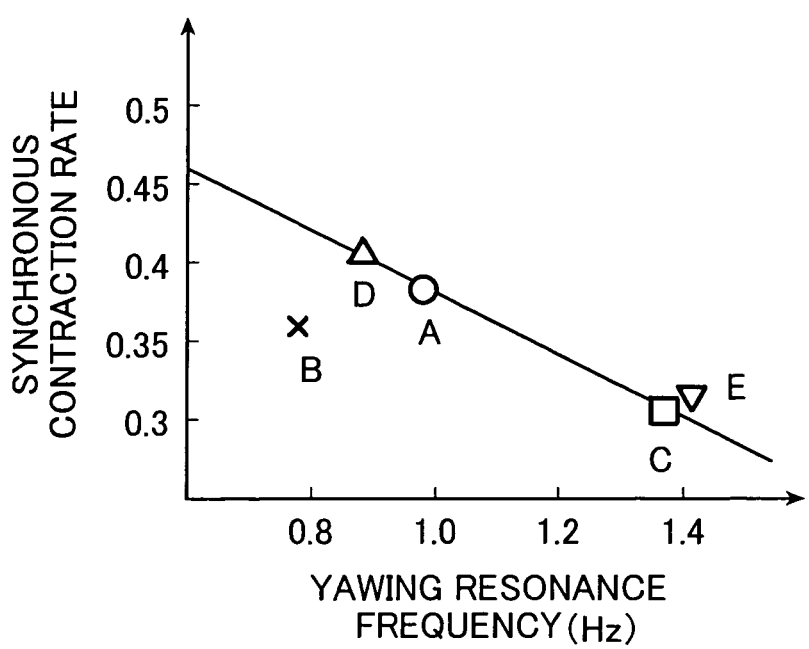
FIG. 6 is a scatter diagram showing a relationship between the results of the synchronous contraction rates calculated by the steering comfort evaluating device shown in FIG. 1 and a yawing resonance frequency.

FIG. 6 is a scatter diagram showing a relationship between a yawing resonance frequency as a vehicle characteristic and a synchronous contraction rate obtained in the manner mentioned above. The yawing resonance frequencies were obtained for all the five test specifications A to E. The yawing resonance frequency is one of factors which affect the steering performance of the vehicle. As the yawing frequency becomes higher, a vehicle responds to the steering operation faster and more stably, putting less mental burden on the driver. Therefore, as the yawing frequency becomes higher, a level of steering comfort becomes higher.

As seen from FIG. 6, as the yawing frequency becomes higher, the synchronous contraction rate becomes smaller, except in the test specification B. From this fact, it is generally seen that the synchronous contraction rate indicates easiness of the steering operation by the driver, that is, an index indicating a level of mental stress at the time of steering.

Figure 7A:
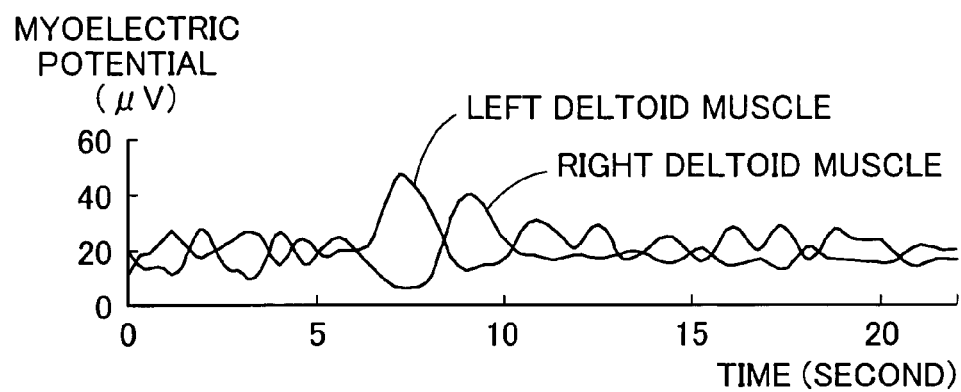
FIG. 7A is a graph showing examples of waveforms of myoelectric potentials at right and left deltoid muscles calculated by the steering comfort evaluating device shown in FIG. 1.
Figure 7B:
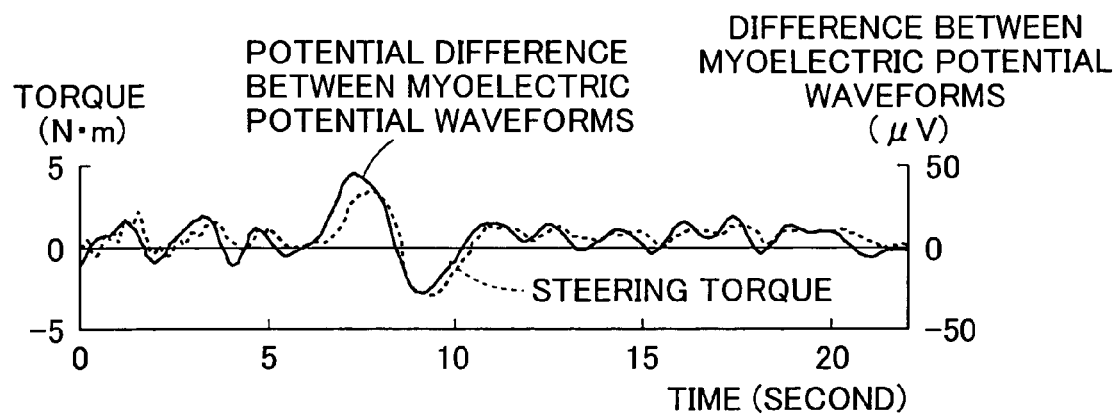
FIG. 7B is a graph showing a relationship between a potential difference between two myoelectric potential waveforms shown in 7A and a waveform of a steering torque.

FIG. 7A is a graph showing waveforms of myoelectric potentials at the right and left deltoid muscles when the vehicle changes traffic lanes on the road. As seen from FIG. 7A, the myoelectric potential waveforms of the right and left deltoid muscles antagonistically act (when one of the deltoid muscles contracts, the other relaxes). FIG. 7B is a graph showing a relationship between a potential difference between the myoelectric potential waveforms at the right and left deltoid muscles, and a steering torque variation of the steering wheel measured when it is actually turned. As clearly seen from the graph, a variation of the steering torque resembles a variation of the potential difference between the myoelectric potential waveforms at the right and left deltoid muscles. From the graph, it is seen that the steering wheel is turned through the antagonistic activities of the right and left deltoid muscles, and that the myoelectric potential waveform reflects physical quantities, e.g., a steering torque indicating a motion of the steering wheel. Therefore, the steering torque measured may be used as an index of an intensity of work load imparted to the deltoid muscles. A steering energy in the steering operation done by the driver, which is obtained by multiplying the steering torque by the steering angular velocity, may also be used as an index of the work load intensity. Further, physical quantities such as a yaw rate indicating a dynamic behavior of the vehicle, which is generated by the steering operation, and a lateral acceleration, may be used as an index of the work load intensity.

As described above, in the present invention, a level of mental stress at work can be properly evaluated by dividing a synchronous contraction intensity of the muscles when one piece of work is done through cooperative actions of plural muscles that antagonistically act, by a work load intensity concurrently calculated.

While the work comfort evaluating device and the work comfort evaluating method, which are implementations of the present invention, have been described in detail, it should be understood that the invention is not limited to those implementations, but may variously be modified, altered, and changed within the true spirits of the invention.

What is claimed is:

1. A work comfort evaluating device for evaluating a level of comfort of work by measuring myoelectric potentials of muscles when the work is done by antagonistic activities of said muscles, said work comfort evaluating device comprising:
   a pair of detecting sensors for sensing myoelectric potentials generated through muscular activities of a human body at a time of work of said muscles;
   an amplifier for amplifying said myoelectric potentials sensed by said detecting sensors;
   a signal processing part for calculating a synchronous contraction intensity of said muscles by using myoelectric potential waveforms of said amplified myoelectric potentials, wherein the signal processing part is configured to calculate a geometrical average of said myoelectric potential waveforms of said muscles, and is further configured to calculate the root mean square values of the calculated geometrical average within a predetermined period, and wherein the device is configured to use the calculated root mean square values as the synchronous contraction intensity;
   a work load intensity calculating part for calculating a level of a work load intensity in said work imparting load to said muscles, said device configured to calculate the level of said work load intensity together with calculating said synchronous contraction intensity; and
   an evaluation part for evaluating a level of comfort of said work by normalizing said synchronous contraction intensity by dividing the synchronous contraction intensity by the calculated level of said work load intensity,
   wherein said work load intensity calculating part is configured to calculate the level of the work load intensity from the myoelectric potential waveforms of said muscles.

2. The work comfort evaluating device according to claim 1, wherein said muscles are a pair of muscles located at right and left parts of the human body.

3. The work comfort evaluating device according to claim 2, wherein said pair of muscles are deltoid muscles of a shoulder of the human body.

4. The work comfort evaluating device according to claim 1, wherein said work load intensity calculating part is configured to calculate the intensities of muscular loads imparted to said muscles in said work from the myoelectric potential waveforms of said muscles, and is further configured to average and smooth the calculated muscular load intensities in an averaging process to thereby calculate the level of said work load intensity.

5. The work comfort evaluating device according to claim 4, wherein said averaging process is a geometric averaging process.

6. The work comfort evaluating device according to claim 1, wherein said work is a work in which said muscles cooperate to cause an object to be operated to dynamically behave, and said work load intensity calculating part is configured to calculate the level of said work load intensity by measuring a physical quantity representing a dynamic behavior of said object operated by the work.

7. The work comfort evaluating device according to claim 1, wherein said work is a driving of a vehicle that is performed by a driver turning a steering wheel.

8. The work comfort evaluating device according to claim 1, wherein said signal processing part is configured to sample time-series data of the myoelectric potentials of the muscles to generate the myoelectric potential waveforms.

9. The work comfort evaluating device according to claim 4, wherein said workload intensity calculating part is configured to obtain the muscular load intensity by calculating the root mean square values of the myoelectric potential waveform of said muscles within the same period of time when the root mean square values used as the synchronous contraction intensity are calculated.

10. The work comfort evaluating device according to claim 4, wherein the work load intensity calculating part is configured to obtain the work load intensity by calculating separately the muscular load intensities of the muscles.

11. The work comfort evaluating device according to claim 1, wherein the evaluation part is configured to calculate a synchronous contraction rate, which represents a level of mental stress by using the synchronous contraction intensities of the muscles and is configured to evaluate the level of comfort of the work based on the synchronous contraction rate.

12. The work comfort evaluating device according to claim 1, wherein the evaluation part is configured to compare the synchronous contraction rate with preset values for the respective ranks to evaluate the level of comfort of the work.

13. A work comfort evaluating method for evaluating a level of comfort of a work by measuring myoelectric potentials of muscles when the work is done by antagonistic activities of said muscles, said work comfort evaluating method comprising:

sensing and amplifying myoelectric potentials of said muscles, said myoelectric potentials being generated through muscular activities of a human body at a time of work;

calculating a geometrical average of said myoelectric potential waveforms of said muscles, calculating root mean square values of the calculated geometrical average within a predetermined period, and using the calculated root mean square values as a synchronous contraction intensity;

calculating a level of a work load intensity in said work imparting load to said muscles from the myoelectric potential waveforms of said muscles together with the generation of said synchronous contraction intensity; and evaluating a level of comfort of said work by normalizing said synchronous contraction intensity by dividing the synchronous contraction intensity by the calculated level of said work load intensity.

* * * * *